United States Patent [19]

Nishimura et al.

[11] Patent Number: 4,729,992
[45] Date of Patent: Mar. 8, 1988

[54] CEPHALOSPORIN ESTERS, THEIR PRODUCTION AND USE

[75] Inventors: Tatsuo Nishimura; Yoshinobu Yoshimura; Mitsuo Numata, all of Osaka, Japan

[73] Assignee: Tatsuo Chemical Ind., Ltd., Japan

[21] Appl. No.: 724,927

[22] Filed: Apr. 19, 1985

[30] Foreign Application Priority Data

Apr. 20, 1984 [JP] Japan .................. 59-80744

[51] Int. Cl.$^4$ .................. A61K 31/545; C07D 501/36
[52] U.S. Cl. ..................... 514/206; 540/227
[58] Field of Search .................. 544/27; 514/206; 540/227

[56] References Cited

U.S. PATENT DOCUMENTS

| 4,080,498 | 3/1978 | Numata et al. | 544/27 |
| 4,189,479 | 2/1980 | Kakeya et al. | 544/27 |
| 4,497,809 | 2/1985 | Yoshimura et al. | 544/27 |

FOREIGN PATENT DOCUMENTS

| 57422 | 8/1982 | European Pat. Off. | 544/27 |
| 128027 | 12/1984 | European Pat. Off. | 540/227 |
| 2215039 | 10/1972 | Fed. Rep. of Germany | 544/27 |

*Primary Examiner*—Donald G. Daus
*Assistant Examiner*—William A. Teol, Jr.
*Attorney, Agent, or Firm*—Antonelli, Terry & Wands

[57] ABSTRACT

A compound of the formula:

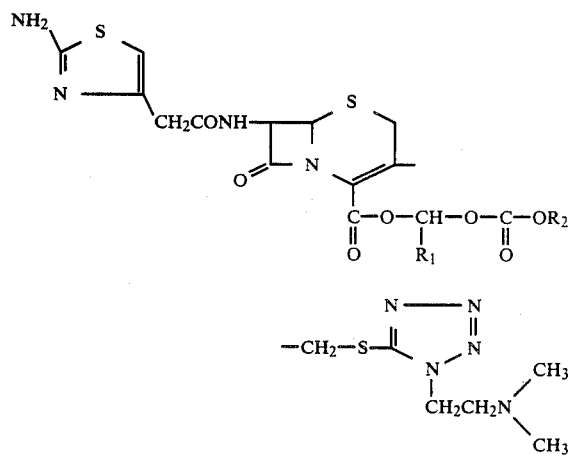

or a pharmaceutical acceptable salt thereof, processes for preparing the same and a pharmaceutical composition containing the compound or the salt thereof mentioned above are provided. The compound has antibiotic activity and has improved absorbability.

5 Claims, No Drawings

CEPHALOSPORIN ESTERS, THEIR PRODUCTION AND USE

This invention relates to compounds of the formula:

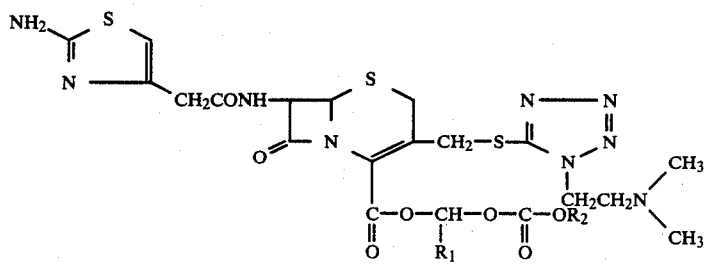

[I]

wherein $R_1$ is a cycloalkyl group; and $R_2$ is a straight-chain, branched or cyclic alkyl group which may optionally be substituted, or pharmaceutically acceptable salts thereof. Said compounds or salts thereof have antibiotic activity and are effective as pharmaceuticals.

For improving the absorbability, on oral administration, of 7β-[2-(2-aminothiazol-4-yl)acetamido]3-[[[1-(2-dimethylaminoethyl)-1H-tetrazol-5-yl]thio]methyl]-ceph-3-em-4-carboxylic acid (described in U.S. Pat. No. 4,080,498, common name: cefotiam, hereinafter referred to briefly as the compound [II]), namely, the non-ester form of the compound [I], it has been suggested to convert the carboxyl group at 4-position of the compound [II] into a straight-chain or branched alkoxy (1 to 5 carbon atoms)carbonyloxy-substituted alkyl ester (e.g. U.S. Pat. No. 4,189,479 and Japanese published unexamined patent application No. 77690/1982). However, these esters have still much to be desired in the respect of absorbability, stability, etc.

The present inventors conducted an intensive study of various ester derivatives of the compound [II] and found that the above novel compound [I] or a salt thereof is efficiently absorbed from the gastrointestinal tract and, after absorption, quickly transferred into the blood stream in the form of non-ester of the compound [I] (i.e. the compound [II]) to establish a high blood level of the compound [II] so that it is of value as an orally administrable broad-spectrum antibiotic displaying potent inhibitory effects not only against β-lactam sensitive gram-positive and gram-negative bacteria, but also against resistant strains thereof. It was also found that the salt of the compound [I] has improved water solubility and a better absorption-efficiency relative to the ester and leads to facilitated procedures of isolation, stabilization of the compound [I] and processing into pharmaceutical preparations of the compound [I].

Referring to the above formula [I], the cycloalkyl group represented by $R_1$ is a cycloalkyl group of 3 to 12 carbon atoms, such as cyclopropyl, cyclobutyl, cyclopentyl, cyclohexyl, cycloheptyl, cyclooctyl, cyclononyl, cyclodecyl, cycloundecyl or cyclododecyl. As for the straight-chain, branched or cyclic alkyl group in the straight-chain, branched or cyclic alkyl group which may optionally be substituted, represented by $R_2$, use is made of a straight-chain or branched alkyl group of 1 to 12 carbon atoms, such as methyl, ethyl, n-propyl, isopropyl, n-butyl, isobutyl, tert-butyl, n-pentyl, isopentyl, neopentyl, tert-pentyl, n-hexyl, isohexyl, heptyl, octyl, nonyl, decyl, undecyl or dodecyl; a saturated monocyclic alkyl group of 3 to 12 carbon atoms, such as cyclopropyl, cyclobutyl, cyclopentyl, cyclohexyl, cycloheptyl, cyclooctyl, cyclononyl, cyclodecyl, cycloundecyl or cyclododecyl; or a bridged cyclic alkyl group of 3 to 12 carbon atoms, such as bicyclo[2.2.1]heptyl, bicyclo[3.2.1]octyl, bicyclo[3.3.1]nonyl or tricyclo[3.3.1.1₃,₇]decyl(adamantyl).

As for the substituents in the straight-chain, branched or cyclic alkyl group which may optionally be substituted, represented by $R_2$, use is made of, for example, acyl, acyloxy, alkoxy, alkoxycarbonyl, optionally substituted hydrocarbon, optionally substituted heterocyclic group, optionally substituted hydrocarbonthio, optionally substituted heterocyclethio, azido, halogen, optionally substituted imino, optionally substituted carbamoylamino, optionally substituted carbamoyl, optionally protected carboxyl, optionally protected hydroxyl or optionally protected amino.

Examples of such substituents are (1) an acyl group, such as ⓐ formyl group, ⓑ a lower alkanoyl group of 2 to 7 carbon atoms, such as acetyl, propionyl, n-butyryl, isobutyryl, n-pentanoyl, n-hexanoyl or n-heptanoyl, ⓒ an arylcarbonyl group, in which the aryl moiety contains preferably 6 to 14 carbon atoms, such as benzoyl, 4-hydroxybenzoyl or 4-methoxybenzoyl, ⓓ aralkylcarbonyl group, in which the aralkyl moiety contains preferably 7 to 10 carbon atoms, such as phenylacetyl, 4-hydroxyphenylacetyl, 4-methoxyphenylacetyl or phenethyl, ⓔ heterocycle-carbonyl group in which the heterocyclic moiety includes a 5- or 6-membered heterocyclic group which contains 1 to 3 heteroatoms, such as sulfur, nitrogen or/and oxygen, such as 2-thenoyl, 2-pyridylcarbonyl or furoyl, ⓕ a heterocycle-acetyl group in which the heterocyclic group includes a 5- or 6-membered heterocyclic group which contains 1 to 3 heteroatoms, such as sulfur, nitrogen or/and oxygen, such as 2-, 4- or 5-thiazolylacetyl, 2- or 3-thienylacetyl, 2- or 3-furylacetyl or 2-amino-4 or 5-thiazolylacetyl; (2) an acyloxy group, such as ⓐ a formyloxy group, ⓑ a lower alkanoyloxy group of 2 to 7 carbon atoms, such as acetoxy, propionyloxy, n-butyryloxy, isobutyryloxy, n-pentanoyloxy, n-hexanoyloxy or n-heptanoyloxy, ⓒ an arylcarbonyloxy group, in which the aryl moiety contains preferably 6 to 14 carbon atoms, such as benzoyloxy, 4-hydroxybenzoyloxy or 4-methoxybenzoyloxy, ⓓ aralkylcarbonyloxy group, in which the aralkyl moiety contains preferably 7 to 10 carbon atoms, such as phenylacetoxy, 4-hydroxyphenylacetoxy, 4-methoxyphenylacetoxy or phenylethyl, ⓔ a heterocycle-carbonyloxy group in which the heterocyclic moiety includes a 5-or 6-membered heterocyclic group which contains 1 to 3 heteroatoms, such as sulfur, nitrogen or/and oxygen, such as 2-thenoyloxy, 2-pyridylcarbonyloxy or 2-furoyloxy, ⓕ a heterocycle-acetoxy group in which the heterocyclic group includes a 5- or 6-membered heterocyclic group which contains 1 to 3 heteroatoms, such as sulfur, nitrogen or/and oxygen, such as 2-, 4- or 5-thiazolylacetoxy, 2- or 3-thienylacetoxy, 2- or 3-furylacetoxy or 2-amino-4 or 5-thiazolylacetoxy; (3) a lower alkoxy group of 1 to 6 carbon atoms, such as methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, n-hexyloxy or isohexyloxy; (4) a lower alkoxycarbonyl group which contains 1 to 6 carbon atoms in the alkoxy moiety, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, n-hexyloxycarbonyl or isohexyloxycarbonyl; (5) hydrocarbon of 1 to 14 carbon atoms (e.g. an aryl group, preferably containing 6 to 14 carbon atoms or a lower alkyl group of 1 to 6 carbon atoms) which may optionally be substituted by ⓐ halogen (e.g. fluorine, chlorine, bromine or iodine) or ⓑ an amino group which may optionally be protected, such as phenyl, α-naphthyl, β-naphthyl, anthryl, 4-fluorophenyl, 2-chlorophenyl, 2,4-dichlorophenyl, 4-bromophenyl, 2-chloro-4-bromophenyl, 4-iodophenyl, 2-chloro-3-bromophenyl, 3-iodophenyl, 4-aminophenyl, 4-acetamidophenyl, methyl, ethyl, n-propyl, isopropyl, n-butyl, isobutyl, tertbutyl, n-pentyl, isopentyl, neopentyl, tert-pentyl, n-hexyl, isohexyl, chloromethyl, aminomethyl or acetamidomethyl, the number of the substituents being 1 to 3; (6) a heterocyclic group, such as a 3- to 8-membered heterocyclic group which contains 1 to 5 heteroatoms, such as nitrogen, oxygen or/and sulfur atoms, and may optionally be fused with a benzene ring and be in the oxide form, such as 1- or 2-aziridinyl, 2- or 3-azetidinyl, 2- or 3-thienyl, 2- or 3-furyl, 2- or 3-pyrrolyl, 2-, 3- or 4-pyranyl, 2-, 3- or 4-thiopyranyl, pyridyl, imidazolyl, pyrazolyl, pyrazinyl, pyrimidinyl, pyridazinyl, quinolyl, isooxazolyl, pyrazolinyl, piperidyl, piperazinyl, 2,3-dioxopiperazinyl, morpholinyl, 2-, 4- or 5-thiazolyl or 2-amino- 4 or 5-thiazolyl; (7) a hydrocarbonthio group of 1 to 14 carbon atoms (e.g. an arylthio group containing preferably 6 to 14 carbon atoms or a lower alkylthio group of 1 to 6 carbon atoms) which may optionally be substituted by ⓐ a halogen (e.g. fluorine, chlorine, bromine or iodine) or ⓑ an amino group which may optionally be protected, such as phenylthio, α-naphthylthio, β-naphthylthio, anthrylthio, 4-fluorophenylthio, 2-chlorophenylthio, 2,4-dichlorophenylthio, 4-bromophenylthio, 2-chloro-3-bromophenylthio, 3-iodophenylthio, 2-chloro-4-bromophenylthio, 4-iodophenylthio, 4-aminophenylthio, 4-acetamidophenylthio, methylthio, ethylthio, n-propylthio, isopropylthio, n-butylthio, isobutylthio, tert-butylthio, n-pentylthio, isopentylthio, neopentylthio, tertpentylthio, n-hexylthio, isohexylthio, chloromethylthio, aminomethylthio or acetamidomethylthio, the number of the substituents being 1 to 3; (8) a heterocyclethio group in which the heterocyclic moiety includes a 4- to 8-membered heterocyclic group which contains 1 to 5 heteroatoms, such as nitrogen, oxygen or/and sulfur atoms, and may optionally be fused with a benzene ring and be in the oxide form, such as 2- or 3-thienylthio, 2- or 3-furylthio, 2- or 3-pyrrolylthio, 2-, 3- or 4-pyranylthio, 2-, 3- or 4-thiopyranylthio, pyridylthio, imidazolylthio, pyrazolylthio, pyrazinylthio, pyrimidinylthio, pyridazinylthio, quinolylthio, isooxazolylthio, pyrazolinylthio, piperidylthio, piperazinylthio, 2,3-dioxopiperazinylthio, morpholinylthio, 2-, 4- or 5-thiazolylthio or 2-amino-4 or 5-thiazolylthio; (9) an azido group, (10) a halogen, such as fluorine, chlorine, bromine or iodine, (11) an imino group which may optionally be substituted by a lower alkyl group of 1 to 6 carbon atoms, such as imino, methylimino, ethylimino, n-propylimino, isopropylimino, n-butylimino, isobutylimino, sec-butylimino, tert-butylimino, n-pentylimino, isopentylimino, n-hexylimino or isohexylimino; (12) a carbamoylamino group which may optionally be substituted by (a) a phenyl group or (b) a lower alkyl group of 1 to 6 carbon atoms, such as carbamoylamino, (N-methylcarbamoyl)amino, (N-ethylcarbamoyl)amino, (N,N-diethylcarbamoyl)amino, (N-propylcarbamoyl)amino, (N,N-dibutylcarbamoyl)amino or (N-n-hexylcarbamoyl)amino, the number of the substituents being 1 to 2; (13) a carbamoyl group which may optionally be substituted by a lower alkyl group of 1 to 6 carbon atoms, such as carbamoyl, N-methylcarbamoyl, N-ethylcarbamoyl, N,N-dimethylcarbamoyl, n-pentylcarbamoyl or isohexylcarbamoyl, the number of the substituents being 1 to 2; (14) a carboxyl group which may optionally be protected; (15) a hydroxyl group which may optionally be protected; or (16) an amino group which may optionally be protected. One to three of these groups may be present on the straight-chain, branched or cyclic alkyl group.

Of these, $R_1$ is preferably a cycloalkyl group of 3 to 7 carbon atoms, such as cyclopropyl, cyclobutyl, cyclopentyl, cyclohexyl or cycloheptyl and $R_2$ is a straight-chain or branched alkyl group of 1 to 6 carbon atoms, such as methyl, ethyl, n-propyl, isopropyl, n-butyl, isobutyl, tert-butyl, n-pentyl, isopentyl, neopentyl, tert-pentyl, n-hexyl or isohexyl, or a saturated monocyclic alkyl group of 3 to 7 carbon atoms, such as cyclopropyl, cyclobutyl, cyclopentyl, cyclohexyl or cycloheptyl. Most preferably $R_1$ is a cycloalkyl group of 5 to 6 carbon atoms, such as cyclopentyl or cyclohexyl and $R_2$ is a straight-chain or branched alkyl group of 1 to 6 carbon atoms, such as methyl, ethyl, n-propyl, isopropyl, n-butyl, isobutyl, tert-butyl, n-pentyl, isopentyl, neopentyl, tert-pentyl, n-hexyl or isohexyl, or a saturated monocyclic alkyl group of 5 to 6 carbon atoms, such as cyclopentyl or cyclohexyl.

As protective groups for the amino group mentioned above, those groups which can be used for this purpose in the synthesis of β-lactam and peptides may also be used. Examples of these protective groups include an aromatic acyl group, such as phthaloyl, p-nitrobenzoyl or p-tert-butylbenzoyl; an aromatic sulfonyl group, such as p-tert-butylbenzenesulfonyl, p-toluenesulfonyl or benzenesulfonyl; an aliphatic acyl group, such as formyl, acetyl, propionyl, aminoacetyl, N-methylaminoacetyl, monochloroacetyl, dichloroacetyl, trichloroacetyl, trifluoroacetyl, maleoyl or succinyl; an aliphatic sulfonyl group, such as methanesulfonyl or ethanesulfonyl; an esterified carboxyl group, such as methoxycarbonyl, ethoxycarbonyl, t-butoxycarbonyl, isopropoxycarbonyl, 2-cyanoethoxycarbonyl, 2,2,2-trichloroethoxycarbonyl, 2-trimethylsilylethoxycarbonyl, benzyloxycarbonyl, 2-methylsulfonylethoxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl or phenoxycarbonyl; and those groups other than the acyl group, such as trityl, 2-nitrophenylthio, benzylidene, 4-nitrobenzylidene, tri-(lower alkyl group of 1 to 6 carbon atoms)silyl, such as triethylsilyl or methyldiethylsilyl, benzyl or p-nitrobenzyl, tert-butyl, neopentyl. One to two of these groups may optionally be substituted on the amino group. There is no limitation in the selection of these protective groups in this invention.

As protective groups for the carboxyl group, any of those groups which can be used as protective groups for carboxyl group in the synthesis of β-lactam compounds and in the field of organic chemistry may be used. Examples of those include among others ester residues or a silyl ester residue, such as methyl, ethyl, n-propyl, isopropyl, tert-butyl, tertamyl, benzyl, p-nitrobenzyl, o-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, 2-methylsulfonylethyl, 2-trimethylsilylethyl, methylthiomethyl, trityl, 2,2,2-trichloroethyl, 2-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di(-tert-butyl)-4-hydroxybenzyl, mesylmethyl, benzenesulfonylmethyl, phenylthiomethyl, iminomethylaminoethyl, 1-iminoethylaminoethyl, dimethylaminoethyl, pyridine-1-oxide-2-methyl, methylsulfinylmethyl, bis(p-methoxyphenyl)methyl or 2-cyano-1,1-dimethylethyl.

As protective groups for the hydroxyl group, any of those which can be used as protective groups for hydroxyl group in the fields of β-lactam and organic chemistry may be used. Examples of those include among others an acyl group, such as acetyl or chloroacetyl; esterified carboxyl group, such as 2,2,2-trichloroethoxycarbonyl or 2-trimethylsilylethoxycarbonyl; an ether residue, such as tert-butyl, benzyl, p-nitrobenzyl, trityl, methoxymethyl, methylthiomethyl or β-methoxyethoxymethyl; a silyl ether residue, such as trimethylsilyl or tert-butyldimethylsilyl; an acetal residue, such as 2-tetrahydropyranyl or 4-methoxy-4-tetrahydropyranyl, or sulfo. In the selection of these protective groups, there is no special limitation as in the cases for the amino group and the carboxyl group in this invention.

Since the compound [I] is basic in itself, it can be converted into an acid addition salt thereof. Generally, the compound [I] forms an acid addition salt with 1 or 2 mole equivalents of an acid. Acids which are preferably employed for the formation of such acid addition salts include those known to form pharmaceutically acceptable salts with pencillins and cephalosporins; for example, an inorganic acid, such as hydrochloric acid, sulfuric acid or phosphoric acid, and an organic acid, such as maleic acid, acetic acid, citric acid, succinic acid, tartaric acid, malic acid, malonic acid, fumaric acid, benzoic acid, mandelic acid, ascorbic acid or methanesulfonic acid.

Preferred salts of the compound [I] are the monohydrochloride and dihydrochloride. The most desirable one is the dihydrochloride. The aminothiazole group of the compound [I] or a salt thereof may exist in the form of its tautomer i.e. iminothiazoline. As the compound [I] or a salt thereof has an asymmetric carbon in the carboxyl ester group at 4-position of the cephem nucleus, there exist two optically active forms (D-isomer and L-isomer). The compound [I] or a salt thereof can generally be used as a racemic compound but either the D-isomer or L-isomer or mixtures of such optical isomers at any ratio can also be employed. The compound [I] or a salt thereof is absorbed well through the gastrointestinal tract and then, after absorption, the ester moiety at its 4-carboxyl position is promptly hydrolyzed with enzyme in the body to give the non-ester form of the compound [I], i.e., the compound [II].

The compound [II] has strong antibacterial activity as mentioned in Antimicrobial Agent and Chemotherapy 14, 557–568 (1978). Thus, the compound [II] shows potent antibacterial activity against grampositive bacteria, such as *Staphylococcus aureus* and gram-negative bacteria, such as *Escherichia coli, Klebsiella pneumoniae, Proteus vulgaris, Proteus mirabilis* or *Proteus morganii.*

Since the compound [I] or a salt thereof, when administered by the oral route, gives a high concentration of the compound [II] in the blood, it is useful for the treatment of infections due to said bacteria in man and other mammalian animals, such as respiratory tract and urinary tract infections due to said bacteria.

The compound [I] or a salt thereof is of low toxicity ($LD_{50} \geq 3$ g/kg, mice, p.o.) and can be orally administered. Therefore, in combination with per se known pharmaceutically acceptable excipients (e.g. starch, lactose, calcium carbonate, calcium phosphate), binders (e.g. starch, gum arabic, carboxymethylcellulose, hydroxypropylcellulose, crystalline cellulose), lubricants (e.g. magnesium stearate, talc) or/and disintegrating agents (e.g. carboxymethylcellulosecalcium, talc), the compound [I] or a salt thereof can be formulated into dosage forms, such as capsules, powders, fine granules, granules or tablets. It is also possible to add about 1 to 5 mole equivalents of a solid organic acid (e.g. citric acid, malic acid, tartaric acid, succinic acid, ascorbic acid or mandelic acid) to the compound [I] or a salt thereof and mold the mixture into granules in a conventional manner. Such granules can be further processed into capsules, tablets, etc. by the established pharmaceutical procedures.

With regard to the dosage regimen, the compound [I] or a pharmaceutically acceptable salt thereof is safely and effectively administered at a daily dose of 0.3 to 5 g per adult human, preferably 0.5 to 3 g per adult human divided into 3 or 4 equal doses.

The compound [I] or a salt thereof can be produced by per se known processes (for example, the processes described in U.S. Pat. Nos. 4,080,498, 4,189,479 or Japanese published unexamined patent application No. 77690/1982). Moreover, the compound [I] or a salt thereof can be produced by esterifying the compound [II] or a salt thereof with a compound of the formula:

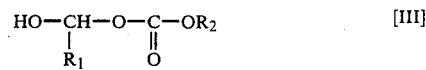

$$HO-\underset{R_1}{CH}-O-\underset{O}{\overset{\|}{C}}-OR_2 \quad [III]$$

wherein $R_1$ and $R_2$ have the same meaning as defined above, or a reactive derivative thereof, according to a conventional manner.

The reactive derivative is for example a compound of the formula:

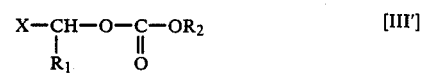

$$X-\underset{R_1}{CH}-O-\underset{O}{\overset{\|}{C}}-OR_2 \quad [III']$$

wherein X is a halogen; $R_1$ and $R_2$ have the same meaning as defined above.

Referring to the above formula [III'], the halogen atom represented by X is, for example, chlorine, bromine or iodine. Of these species, preferably X is iodine.

As the compounds [III] and [III'] have an asymmetric carbon atom, it can be optically resolved into D- and L-isomers by a per se known procedure and either of the isomers or a mixture thereof can be used in the contemplated esterification reaction.

The starting compound [II] can be subjected to the reaction in the form of an acid addition salt with an inorganic acid, such as hydrochloric acid, sulfuric acid or nitric acid, or an organic acid, such as oxalic acid or p-toluenesulfonic acid, or in the form of a salt with a base, such as an alkali metal, e.g. sodium or potassium, an alkaline earth metal, e.g. calcium or magnesium, or an organic amine, e.g. triethylamine, trimethylamine, pyridine, collidine or lutidine.

In conducting the esterification reaction, the starting compound [III] or [III'] is used in a proportion of about 1 to 10 mole equivalents to each equivalent of the starting compound [II] or a salt thereof. This reaction is generally carried out in a solvent inert to the reaction. Examples of a solvent include among others amides, such as N,N-dimethylformamide (hereinafter referred to briefly as DMF), N,N-dimethylacetamide (hereinafter referred to briefly as DMAC) or hexamethylphosphorotriamide (hereinafter referred to briefly as HMPA), halogenated hydrocarbons, such as dichloromethane or chloroform, sulfoxides, such as dimethyl sulfoxide (hereinafter referred to briefly as DMSO) or sulfolane, ethers, such as dioxane or tetrahydrofuran (hereinafter referred to briefly as THF), ketones, such as acetone or methyl ethyl ketone, nitriles, such as acetonitrile, or liquefied sulfur dioxide. Preferred are DMF, DMAC, HMPA, acetone, acetonitrile and liquefied sulfur dioxide. This esterification reaction is conducted generally at a temperature between about −20° C. and 20° C. While the reaction can be conducted in the absence of a catalyst, a catalyst, such as a phase transfer catalyst (e.g. 18-crown-6, etc.) can be employed. When liquefied sulfur dioxide is used as the solvent, the reaction is preferably conducted at a temperature near the boiling point (−10° C.) of the solvent, i.e. about −10° C. to −20° C. The reaction time is generally a few minutes to about one hour, depending on the reactants and solvent employed.

The compound[I] or a salt thereof can also be produced by the following processes. Thus, a compound of the formula:

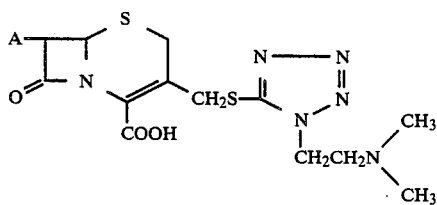

wherein A is an amino group or an acylamino group other than 2-(2-aminothiazol-4-yl)acetylamino, or a salt thereof is reacted with the compound [III'] in the same manner as described in the above esterification reaction. When A is an acylamino group, the resulting ester is reacted with phosphorus pentachloride and, then, with alcohol (e.g. methanol, ethanol, propanol, isopropanol or n-butanol) [the process described in Journal of Medicinal Chemistry 18, 992 (1975), and West German Laid-open Patent Application Nos. 2460331 and 2460332]. The resulting compound of the formula:

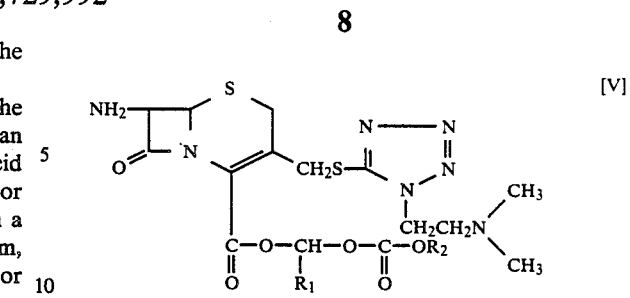

wherein symbols have the same meaning as defined above, or a salt thereof is acylated with a compound of the formula:

wherein $R_3$ is an amino group or a protected amino group, or a reactive derivative thereof, if necessary followed by removing the protective group, to give the compound [I] or a salt thereof. The compound [IV] or a salt thereof can be produced according to the same procedure as described in e.g. U.S. Pat. Nos. 4,080,498 and 4,098,888.

When A is an acylamino group in the above formula [IV], the acyl group can be any of the acyl groups known per se in the field of cephalosporin compounds. Preferred acylamino groups are acetylamino, benzoylamino, phenylacetylamino, thienylacetylamino, phenoxyacetylamino and 5-amino-5-carboxyvalerylamino (the substituent amino group may be protected with phthaloyl or the like). When A is an amino group or an amino-substituted acylamino group, the amino group is preferably protected before the reaction and as the protective group therefor, use is made of a per se known protective group for an amino group, such as t-butoxycarbonyl, benzyloxycarbonyl, 2-hydroxy-1-napthocarbonyl, trichloroethoxycarbonyl, 2-ethoxycarbonyl-1-methylvinyl, or 2-methoxycarbonyl-1-methylvinyl, chloroacetyl, formyl, trifluoroacetyl or trityl.

The compound [IV] can be subjected to the reaction in the form of an acid addition salt with an inorganic acid, such as hydrochloric acid, sulfuric acid or nitric acid, or an organic acid, such as oxalic acid or p-toluenesulfonic acid, or in the form of a salt with a base, such as an alkali metal, e.g. sodium or potassium; alkaline earth metal, e.g. calcium or magnesium; or an organic amine, e.g. triethylamine, trimethylamine, pyridine, collidine or lutidine.

The deacylation of the ester compound produced by reacting the compound [IV] (when A is an acylamino group) with the compound [III'] is conducted in a per se known manner, using generally about 2 to 5 mole equivalents of phosphorus pentachloride and about 10 to 40 mole equivalents of alcohol per mole of the starting ester compound. This reaction is generally conducted in a solvent inert to the reaction. Examples of the solvent include halogenated hydrocarbons, such as dichloromethane or chloroform. For the purpose of accelerating the reaction, a tartiary amine, such as triethylamine, pyridine or N,N-dimethylaniline may be added to the reaction system. The reaction temperature is about −40° C. to about −20° C. The reaction time is usually about 1 hour.

When the resulting compound [V] or a salt thereof is reacted with the compound [VI] or a reactive derivative thereof, to produce the compound [I] or a salt thereof, the amino group of the compound [VI] is preferably protected beforehand, and the protective group in the protected amino group represented by $R_3$ can be similar to the protective group for the amino group of the compound [IV]. The protected amino group represented by $R_3$ may be a group of the formula:

$NH_3^{\oplus}$— wherein $Z^{\ominus}$ is anion. The examples of anion represented by $Z^{\ominus}$ include halogen anion, sulfate anion etc. The halogen represented by Z is for example chlorine, bromine or iodine.

The compound [V] can be subjected to the reaction in the form of an acid addition salt with an inorganic acid, such as hydrochloric acid, sulfuric acid or nitric acid, or an organic acid, such as oxalic acid or p-toluenesulfonic acid. In this reaction, the compound [VI] may be used in the form of a reactive derivative. Thus, for example, it is subjected to said acylation reaction in the form of the corresponding acid halides, acid anhydrides, mixed acid anhydrides, active amides, active esters, etc. Preferred are the active esters, mixed acid anhydrides, acid halides, etc. Examples of the active esters include p-nitrophenyl ester, 2,4-dinitrophenyl ester, pentachlorophenyl ester, N-hydroxyphthalimide ester, and the ester formed by means of a Vilsmeier or similar reagent and so on. The mixed acid anhydrides are those prepared from the compound [VI] and carbonic mono esters, such as monomethyl carbonate, monoisobutyl carbonate, etc., and those prepared from the compound [VI] and alkanoic acids of 2 to 5 carbon atoms which may be substitued by halogens, such as pivalic acid, trichloroacetic acid, etc. Examples of the acid halides are acid chloride, acid bromide etc. In this reaction, the compound [VI] or a reactive derivative thereof is used in a proportion of about 1 to 2 mole equivalents to each mole of the compound [V] or a salt thereof.

When the compound [VI] is used in the form of the free acid or a salt thereof, a suitable condensing agent is employed. Examples of the condensing agent include N,N'-di-substituted carbodiimides, such as N,N'-dicyclohexylcarbodiimide, azolides, such as N,N'-carbonylimidazole or N,N'-thionyldiimidazole, and dehydrating agents, such as N-ethoxycarbonyl-2-ethoxy-1,2-dihydroquinoline, phosphorus oxychloride or alkoxyacetylenes (e.g. ethoxyacetylene). When the condensing agent is employed, the reaction appears to proceed via formation of a reactive derivative of the carboxylic acid.

The reaction can generally be conducted smoothly in a solvent. Examples of the solvent include the common solvents which do not interfere with the reaction to produce compound [I], such as water, acetone, diisobutyl ketone, THF, ethyl acetate, dioxane, acetonitrile, chloroform, dichloromethane, dichloroethylene, pyridine, dimethylaniline, DMF, DMAC or DMSO, as well as mixtures of such solvents. While the reaction temperature is virtually optional, the reaction is usually conducted at about −20° C. to 20° C. When the reaction proceeds with liberation of an acid, a base is added to the reaction system if necessary. The base used for this purpose is exemplified by aliphatic, aromatic or heterocyclic nitrogencontaining bases, such as triethylamine, N,N-dimethylaniline, N-ethylmorpholine, pyridine, collidine or 2,6-lutidine; alkali metal carbonates, such as sodium carbonate or potassium carbonate, or alkali metal bicarbonate, such as potassium hydrogen carbonate or sodium hydrogen carbonate. When the acylation reaction proceeds with dehydration, it is preferable to remove water from the solvent. In some instances, the reaction may be conducted under moisture-free conditions in an atmosphere of an inert gas such as nitrogen.

When the reaction product has a protective group, the protective group is removed by a per se known procedure (e.g. the procedure described in U.S. Pat. No. 4,080,498).

The compound [I] or a salt thereof can also be produced by the following procedure. Thus, the compound [V], or a salt thereof is reacted with a 4-halo-3-oxobutyryl halide, which is obtained by reacting diketene with a halogen (e.g. chlorine or bromine) in an equimolar ratio, to give a compound of the formula:

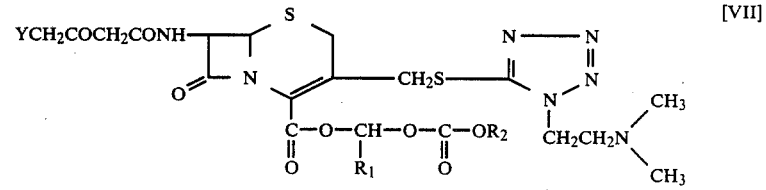

[VII]

wherein Y is a halogen atom; $R_1$ and $R_2$ have the same meaning as defined above, or a salt thereof, which is then reacted with thiourea. In the above formula [VII], the halogen atom Y is for example chlorine or bromine.

The reaction of the compound [V], or a salt thereof with 4-halo-3-oxobutyryl halide may be carried out by methods known per se, e.g., the method disclosed in U.S. Pat. No. 4080498.

In the reaction of the compound [VII], or a salt thereof with thiourea, thiourea is preferably used as it is, but may be used in the form of a salt with an alkali metal, such as lithium, sodium or potassium, or ammonium salt. The reaction is generally carried out using the two reactants in an equimolar ratio in a solvent. Preferred examples of the solvent include water, a hydrophilic solvent, such as methanol, ethanol, acetone, dioxane, acetonitrile, chloroform, ethylene chloride, THF, ethyl acetate, DMF, DMAC or DMSO, etc. Among these solvents, a hydrophilic solvent can be used in admixture with water. Alternatively, the reaction may be conducted in the presence of 1 to 2 molar equivalents of a base, if necessary. Preferred examples of the base include alkali metal hydroxides, such as sodium hydroxide or potassium hydroxide, alkali metal carbonates, such as sodium carbonate or potassium carbonate, alkali metal hydrogen carbonates, such as sodium hydrogen carbonate, organic tertiary amines, such as triethylamine, trimethylamine or pyridine. While there is virtually no limitation to the reaction temperature, the reaction is preferably conducted at about −20° C. to 10° C. The reaction proceeds at a fast rate and usually goes to completion within 10 minutes, although a reaction time in excess of 30 minutes is at times required. The compound

[VII] can be easily produced by the above-described process. It can also be prepared by some other processes known per se.

The compound [I] or a salt thereof can also be produced by reacting a compound of the formula:

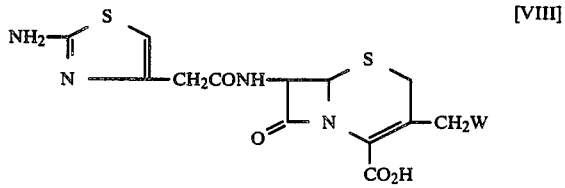

wherein W is acetoxy, acetoacetoxy, a halogen or carbamoyloxy, or a salt thereof with the compound [III] or a reactive derivative thereof, preferably the compound [III'], in the same manner as the esterification reaction described hereinbefore and reacting the resulting compound of the formula:

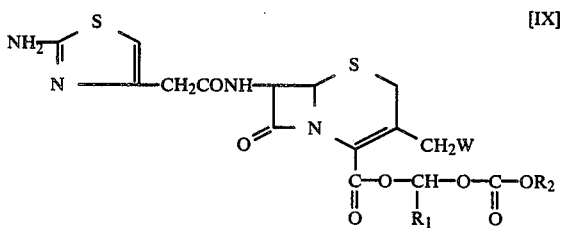

wherein symbols have the same meaning as defined above, or a salt thereof with 1-(2-dimethylaminoethyl)5-mercapto-1H-tetrazole. Referring to the above formulas [VIII] and [IX], the halogen represented by W is, for example, chlorine, bromine or iodine. The compound [VIII] or a salt thereof can be produced according to the same method as described in U.S. Pat. No. 4080498. The salt of the compound [VIII] can be similar to that of the compound [IV], and the salt of compound [IX] can be similar to that of the compound [V]. In this reaction, the starting material 1-(2-dimethylaminoethyl)-5-mercapto-1H-tetrazole is used in an approximately equimolar proportion with respect to the compound [IX].

This reaction can generally be conducted smoothly in a solvent. Examples of the solvent include water, acetone, THF, ethyl acetate, dioxane, acetonitrile, chloroform, dichloromethane, DMF, DMAC, DMSO, etc. When water is used, it can be used in admixture with a highly water-miscible solvent, such as THF, ethyl acetate, dioxane, DMF, DMAC or DMSO. This reaction is usually conducted in the presence of a base. Preferred examples of the base are weak bases, such as alkali metal carbonates (e.g. sodium carbonate or potassium carbonate) and alkali metal bicarbonates (e.g. sodium hydrogen carbonate or potassium hydrogen carbonate). The base is used in an approximately equimolar proportion with respect to the starting compound, 1-(2-dimethylaminoethyl)-5-mercapto-1H-tetrazole.

While the reaction temperature is more or less optional, the reaction is generally conducted at room temperature (about 15° to 20° C.) up to 40° C. through 60° C. The reaction time is about 30 minutes to about 3 hours, depending on the solvent and the reaction temperature employed.

If the compound [I] or a salt thereof prepared as above contains its $\Delta^2$-isomer, the isomer can be converted to the compound [I] or a salt thereof by, for example, isomerizing the $\Delta^2$-isomer to the $\Delta^3$-isomer by a per se known method [Journal of Medicinal Chemistry, Vol. 18, 986 (1975)], or converting the $\Delta^2$-isomer to the corresponding S-oxide derivative and then reducing the product thus obtained.

When the product compound [I] is produced in the form of free compound, it can be converted to a salt thereof by dissolving the free compound in an inert solvent, such as dichloromethane or chloroform, and adding about 1 to 10 mole equivalents of an acid to the solution. When the compound [I] is produced in the form of a salt, it can be converted to the form of free compound according to a per se known procedure. When the compound [I] or a salt thereof is produced in the form of a racemic compound, it can be subjected to the optical resolution according to a per se known procedure to isolate the optically active compounds (D- and L-isomers).

When the product compound [I] or a salt thereof has protective group, the protective group can, if necessary, be removed by per se known processes (e.g., the process described in Theodora W. Greene "Protective Groups in Organic Synthesis" published from John Wiley & Sons, New York, 1981). More concretely the deprotection reaction is shown below. When the protective group for the carboxyl group of the compound [I] or salt thereof is a halogenoalkyl group, an aralkyl group, a benzhydryl group or the like, removal of the protective group can be attained by reacting the compound [I] or a salt thereof with a reducing agent. When the protective group for the carboxyl group is a halogenoalkyl group, such as 2,2-dibromoethyl, 2,2,2-trichloroethyl or the like, use is made of preferably zinc and acetic acid as the reducing agent. When the protective group is an aralkyl group, such as benzyl or p-nitrobenzyl, or a benzhydryl group, use is made of hydrogen and a catalyst for the catalytic reduction, such as platinum oxide, platinum black, platinum sponge, palladium-carbon, palladium-black, palladium-barium sulfate, palladium-barium carbonate, reduced nickel, Raney nickel or Urushibara nickel, alkali metal sulfides, such as sodium sulfide or potassium sulfide and so on. When the protective group is o-nitrobenzyl, it can be removed by irradiation with light. When the protective group is a p-methoxybenzyl group, it may be removed by electrolytic reduction. The above reduction reaction is carried out in the presence of a solvent. Examples of the solvent include alcohols, such as methanol or ethanol; ethers, such as tetrahydrofuran or dioxane; a lower fatty acid containing 2 to 7 carbon atoms, such as acetic acid, propionic acid, butyric acid; admixtures of these solvents with water, etc. The reaction is generally carried out at about 0° to 40° C. The reaction time is about 5 minutes to 12 hours.

When the protective groups for the amino group in the compound [I] or a salt thereof are, for example, p-nitrobenzyloxycarbonyl, o-nitrobenzyloxycarbonyl, p-methoxybenzyloxycarbonyl, benzyloxycarbonyl and so on, the protective groups can be removed in the same manner as in the removal of the protective groups for carboxyl group mentioned hereinbefore.

When the protective group for the hydroxyl group is a tri-(lower alkyl group of 1 to 6 carbon atoms)-silyl group, such as tert-butyldimethylsilyl and so on, the group may be removed by reacting the compound with fluoride ion source, such as tetrabutylammonium fluoride or potassium fluoride. Examples of the solvent include ethers, such as tetrahydrofuran or dioxane. The reaction is completed in about 10 to 18 hours at about room temperature.

The resulting compound [I] or a salt thereof can be isolated and purified by per se known procedures, such as solvent extraction, pH adjustment, solvent transformation, crystallization, recrystallization or/and chromatography.

The starting compound [III] is produced by per se known processes (for example, the process described in Great Britain Pat. No. 1426717). The compound [III] can also be produced by the process illustrated below.

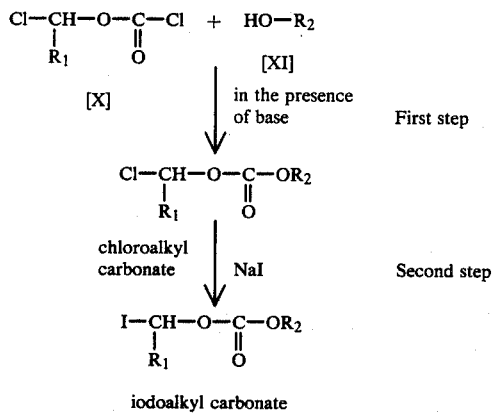

In the above formulas, $R_1$ and $R_2$ have the same meaning as defined above. Chloroformate [X], which is one of the starting compounds in the first step of the reaction in the above equations, is produced by per se known process (for example, European Patent-40153 A). Furthermore, the compound [X] is produced by reacting an aldehyde of the formula $R_1CHO$ wherein $R_1$ has the same meaning as defined above with phosgene in the presence of a catalyst (phosgenation). Examples of the catalyst include tertiary amines, such as N,N-dimethylaniline, N,N-dimethylaminopyridine, or pyridine; aromatic monoamines, such as imidazole; substituted amides, such as DMF; tetra (lower alkyl group of 1 to 4 carbon atoms)ureas, such as tetrabutylurea, tetramethylurea; tetra-(lower alkyl group of 1 to 4 carbon atoms)thioureas, such as tetrabutylthiourea or tetramethylthiourea; aliphatic tertiary phosphines, such as trioctylphosphine; substituted phosphoroamides, such as HMPA. The aldehyde which is the starting compound is used in an approximately equimolar ratio to phosgene. The catalyst can be used in 0.01 to 0.1 mole equivalent to the starting material aldehyde.

The phosgenation is usually conducted in a solvent inert to the reaction. Examples of the solvent include halogenated hydrocarbons, such as carbon tetrachloride, chloroform or methylene chloride; aromatic hydrocarbons, such as toluene or benzene; aliphatic hydrocarbons, such as hexane or petroleum ether.

The phosgenation is usually conducted under atmospheric pressure; however, when the starting material aldehyde is volatile, the reaction may be conducted under a pressure a little higher than the atmospheric pressure.

The reaction temperature depends upon the species of the catalyst and the amount thereof used, varying from approximately −40° C. to 100° C. Reaction time is about 30 minutes to 5 hours.

The compound [X] produced after the completion of this phosgenation can be isolated and purified by per se known procedures, such as concentration or distillation under atmospheric or reduced pressure.

The compound of formula [III'] wherein X is iodine, i.e. iodoalkyl carbonate, is produced by reacting the compound [X] with the compound [XI] in the presence of a base (the first step of the reaction) and reacting the resulting reaction product (chloroalkyl carbonate) with sodium iodine (the second step of the reaction).

In the first step of the reaction, the starting compounds [X] and [XI] are used in an approximately equimolar ratio. This reaction is generally conducted in a solvent inert to the reaction. Examples of a solvent are dichloromethane, chloroform, diethyl ether, ethyl acetate, etc. The base used for this reaction may be an organic tertiary amine, such as pyridine, lutidine, or tri-(lower alkyl group of 1 to 6 carbon atom)amine, e.g. triethylamine or diisopropylethylamine. The base is used in an amount approximately equimolar to the compound [X]. This reaction proceeds at a temperature of −80° C. to 40° C. The reaction time varies depending upon the reaction temperature, for instance, it is generally about 30 minutes to a few days.

The reaction mixture obtained above is subjected to washing with water, extraction, concentration, distillation, column chromatography or/and the like, and the resulting chloroalkyl carbonate is reacted with sodium iodide to give the iodoalkyl carbonate (the second step of the reaction).

The amount of sodium iodide used in the above second step of the reaction is about 1 to 10 mole equivalents with respect to chloroalkyl carbonate. This step of the reaction is conducted in the presence of a common solvent, such as acetone, acetonitrile, DMF or DMSO.

The reaction proceeds at room temperature (about 15° to 20° C.) to about 70° C. The reaction time is usually about 15 minutes to about 24 hours.

The reaction product can be isolated and purified by per se known procedures, such as solvent extraction, pH adjustment, distillation, distillation under reduced pressure, solvent transformation or chromatography.

The following Reference Examples, Examples, Formulation Examples and Experimental Example are further illustrative but by no means limitative of this invention.

The symbols used in these Reference Examples and Examples have the meanings defined below.

s: singlet; b: broad; d: doublet; d.d: double-doublet; t: triplet; q: quartet; sep: septet; ABq: AB-pattern quartet; m: multiplet; TMS: Tetramethyl silane.

NMR (nuclear magnetic resonance) spectrum was measured using Varian XL-100A, 100 MHz (produced by Varian Associates, U.S.A.) unless otherwise specified.

REFERENCE EXAMPLE 1

Cyclohexylchloromethyl chloroformate

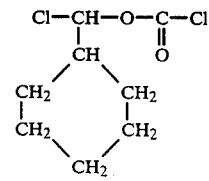

A solution of 28 g of cyclohexanecarbaldehyde

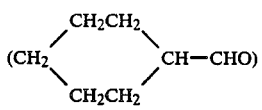

and 1.98 g of pyridine in 50 ml of carbon tetrachloride is cooled to 0° C. and 30 g of phosgene gas is passed through it over a period of one hour. Then, the reaction mixture is warmed up to 34°–40° C. and stirred for one hour at this temperature. Nitrogen gas is passed through the reaction mixture to remove the remaining phosgene. Then, the reaction mixture is filtered and the filtrate is concentrated under reduced pressure. The resultant residue is subjected to distillation under reduced pressure and a fraction boiling at 90°–93° C./10 mmHg is collected to obtain 25 g of the title compound.

IR $\nu_{max}^{liquid\,film}$ cm$^{-1}$: 1780, 1455, 1310, 1240, 1150, 1120

NMR(CDCl$_3$,60 MHz)δ: 0.8–3.0(11H,m), 6.12(1H,d,J=5 Hz)

REFERENCE EXAMPLE 2

Cyclohexylchloromethyl cyclohexyl carbonate

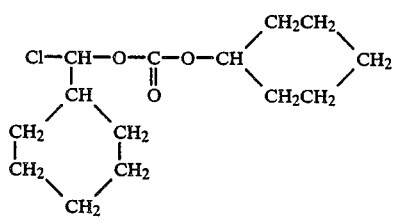

A solution of 2.19 g of cyclohexanol and 1.73 g of pyridine in 70 ml of methylene chloride is cooled to −78° C. and 4.63 g of cyclohexylchloromethyl chloroformate is added dropwise to it over a period of 10 minutes with stirring. After the addition is completed, the cooling bath is removed and the mixture is stirred for 16 hours at room temperature. Then, the reaction mixture is washed three times with 100 ml of a saturated aqueous solution of sodium chloride and dried over anhydrous mangesium sulfate. The solvent is distilled off under reduced pressure to obtain 5.41 g of the title compound as a colorless oil (yield 90%).

IR $\nu_{max}^{liquid\,film}$ cm$^{-1}$: 1760, 1455, 1380, 1360, 1335, 1310, 1250

NMR(CDCl$_3$,60 MHz)δ: 0.8–2.5(21H,m), 4.65(1H, b), 6.10(1H,d,J=5 Hz)

Elemental analysis, for C$_{14}$H$_{23}$ClO$_3$ Calcd.(%): C 61.19; H 8.44; Found (%): C 61.16; H 8.31.

REFERENCE EXAMPLES 3 TO 6

Compounds obtained in the same manner as in Reference Example 2 are shown in Table 1 together with their physico-chemical constants.

TABLE 1

Formula: Cl—CH(R$_1$)—O—C(=O)—O—R$_2$

| Reference Example No. | R$_1$ | R$_2$ | IR$\nu_{max}^{liquid\,film}$ cm$^{-1}$ | NMR (CDCl$_3$,60MHz) δ |
|---|---|---|---|---|
| 3 | cyclohexyl | cyclohexyl | 1760,1455,1380 1325,1310,1260 | 0.8–2.4(19H,m),4.13(1H,b), 6.10(1H,d,J = 5Hz) |
| 4 | cyclohexyl | —CH(CH$_3$)(CH$_2$)$_2$CH$_3$ | 1760,1455,1380 1360,1310,1260 | 1.30(3H,d,J = 7Hz),0.6–2.4(17H, m),4.82(1H,m),6.11(1H,d,J = 5Hz) |
| 5 | cyclohexyl | —C$_2$H$_5$ | 1760,1455,1375 1310,1250 | 1.32(3H,t,J = 7Hz),0.8–2.4(11H, m),4.23(2H,q,J = 7Hz),6.10(1H, d,J = 5Hz) |
| 6 | cyclohexyl | —CH(CH$_3$)$_2$ | 1760,1455,1380 1360,1310,1260 | 1.30(6H,d,J = 7Hz),0.8–2.4(11H, m),4.90(1H,sep,J = 7Hz),6.10(1 H,d,J = 5Hz) |

EXAMPLE 1

(a) Preparation of cyclohexyliodomethyl cyclohexyl carbonate.

A mixture consisting of 5.41 g of cyclohexylchloromethyl cyclohexylcarbonate and 12 g of sodium iodide is stirred in 50 ml of acetonitrile at 60° C. for 60 minutes, followed by concentration under reduced pressure and the resultant residue is partitioned between 100 ml of ether and 100 ml of water. The ether layer is separated and washed with 50 ml of a 5 w/w % aqueous solution of sodium thiosulfate and 100 ml of a saturated aqueous solution of sodium chloride and dried over anhydrous magnesium sulfate. The solvent is distilled off under reduced pressure to obtain the title compound as an oil.

(b) Preparation of cyclohexyloxycarbonyloxy-(cyclohexyl)methyl 7β-[2-(2-aminothiazol-4-yl)acetamido]-3-[[[1-(2-dimethylaminoethyl-1H-tetrazol-5-yl]thio]methyl]ceph-3-em-4-carboxylate dihydrochloride.

In 8 ml of dimethylformamide is dissolved 1.2 g of potassium 7β-[2-(2-aminothiazol-4-yl) acetamido]-3-[[[1-(2-dimethylaminoethyl)-1H-tetrazol-5-yl]thio]methyl]ceph-3-em-4-carboxylate. Under ice-cooling and while stirring, to this solution is added at one stroke 10 ml of a solution of cyclohexyliodomethyl cyclohexyl carbonate obtained in the above (a) in dimethylformamide and the mixture is vigorously stirred for 5 minutes. Then, to the reaction mixture is added 20 ml of a 2N ethereal hydrogen chloride solution and the mixture is stirred for 5 minutes. Thereto is added 150 ml of ether while stirring and the upper layer is removed by decantation (This procedure is repeated twice). The resultant cake is dissolved in 20 ml of 0.1 N hydrochloric acid and subjected to chromatography on a column of Diaion MCI® GEL CHP20P (150-300 μ, Mitsubishi Chemical Industries, Ltd.,Japan), elution being carried out first with 10 v/v % acetonitrile/0.01N hydrochloric acid and then 40 v/v % acetonitrile/0.01N hydrochloric acid. The fractions containing the desired compound are combined, concentrated under reduced pressure and lyophilized to obtain 0.2 g of the title compound as a colorless powder.

Elemental analysis, for $C_{32}H_{45}N_9O_7S_3 \cdot 2HCl \cdot 2.5H_2O$
Calcd.(%): C 43.58; H 5.94; N 14.29; Found (%) C 43.49; H 5.63; N 14.40.

LR $\nu_{max}^{liquid\,film}$ cm$^{-1}$: 1780, 1760, 1660, 1620, 1540, 1450, 1380

NMR(DMSO-$d_6$)δ: 0.8-2.2(21H,m), 2.83(6H,s), 3.64(2H,s), 3.65(2H,t,J=6 Hz), 3.72 and 3.94(2H,ABq,J=18 Hz), 4.24 and 4.50,4.30(2H, each ABq and bs), 4.78(2H,t,J=6 Hz), 4.0-5.0(1H,b), 5.13, 5.16(1H, each d,J=5 Hz), 5.73, 5.77(1H, each d.d,J=5 and 8 Hz), 6.57, 6.63(1H, each d,J=5 Hz), 6.66(1H,s), 9.21, 9.24(1H, each d,J=8 Hz)

EXAMPLES 2 TO 5

The compounds obtained in the same manner as Example 1 are shown in Table 2, together with their physico-chemical constants.

TABLE 2

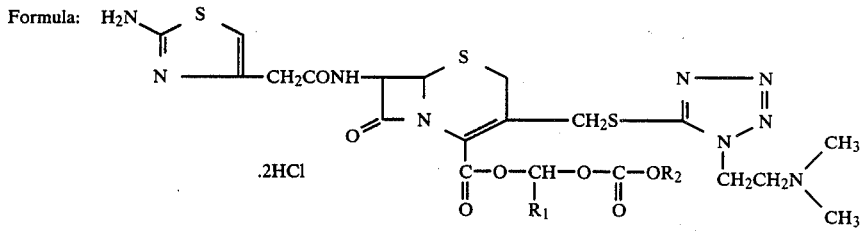

Formula:

| Example No. | $R_1$ | $R_2$ | (A) Elemental analysis<br>(B) IR(KBr)(cm$^{-1}$) | NMR(DMSO—$d_6$) δ |
|---|---|---|---|---|
| 2 | $-CH\begin{smallmatrix}CH_2CH_2\\ \\CH_2CH_2\end{smallmatrix}CH_2$ | $-CH\begin{smallmatrix}CH_2CH_2\\ \\CH_2CH_2\end{smallmatrix}CH_2$ | (A) For $C_{31}H_{43}N_9O_7S_3 \cdot 2HCl \cdot 4H_2O$<br>　　　C　　H　　N<br>Calcd. (%): 41.61　5.97　14.09<br>Found (%): 41.54　5.79　14.53<br>(B) 1780, 1760, 1660, 1625, 1540, 1450, 1380 | 0.8-2.0(19H,m),2.83(6H,s),3.64(2H,s),3.64(2H,t,J=6Hz),3.72 and 3.92(2H,ABq,J=18Hz),4.28 and 4.50,4.31(2H, each ABq and bs,J=13Hz),4.79(2H,t,J=6Hz),5.02(1H,b),5.12,5.16(1H, each d,J=5Hz), 5.72,5.76(1H, each d.d,J=5 and 8Hz),6.56,6.62(1H, each d,J=5Hz),6.66(1H,s),9.22,9.26(1H, each d, J=8Hz) |
| 3 | $-CH\begin{smallmatrix}CH_2CH_2\\ \\CH_2CH_2\end{smallmatrix}CH_2$ | $-CH\begin{smallmatrix}(CH_2)_2CH_3\\ \\CH_3\end{smallmatrix}$ | (A) For $C_{31}H_{45}N_9O_7S_3 \cdot 2HCl \cdot 4H_2O$<br>　　　C　　H　　N<br>Calcd. (%): 41.51　6.24　14.05<br>Found (%): 41.40　5.99　14.41<br>(B) 1780, 1760, 1660, 1620, 1540, 1455, 1380 | 0.86,0.88(3H, each t,J=6Hz),1.22(3H,d,J=6Hz), 0.9-2.0(15H,m),2.84(6H,s),3.64(2H,s),3.64(2H,t),3.71 and 3.91(2H,ABq,J=18Hz),4.27 and 4.51,4.31(2H, each ABq and bs,J=13Hz),4.0-5.0(1H,b),4.79(2H,t, J=6Hz),5.14,5.17(1H, each d,J=5Hz),5.74,5.78(1H, each d.d,J=5 and 8Hz),6.58,6.64(1H, each d,J= 5Hz),6.67(1H,s),9.22,9.26(1H, each d,J=8Hz) |
| 4 | $-CH\begin{smallmatrix}CH_2CH_2\\ \\CH_2CH_2\end{smallmatrix}CH_2$ | $-C_2H_5$ | (A) For $C_{28}H_{39}N_9O_7S_3 \cdot 2HCl \cdot 3.5H_2O$<br>　　　C　　H　　N<br>Calcd. (%): 39.76　5.72　14.90<br>Found (%): 39.70　5.34　15.45<br>(B) 1780, 1760, 1670, 1620, 1530, 1450, 1370 | 0.8-2.0(10H,m),1.23(3H,t,J=7Hz),2.85(6H,s), 3.64(2H,s),3.65(2H,t,J=6Hz),3.73 and 3.92(2H,ABq,J=18Hz),4.16(2H,q,J=7Hz),4.26 and 4.50,4.30(2H, each ABq and bs,J=13Hz),4.79(2H,t, J=6Hz),5.13,5.16(1H, each d,J=5Hz),5.72,5.77(1H, each d.d,J=5 and 8Hz),6.58,6.63(1H, each d,J= 5Hz),6.66(1H,s),9.22,9.26(1H, each d,J=8Hz) |
| 5 | $-CH\begin{smallmatrix}CH_2CH_2\\ \\CH_2CH_2\end{smallmatrix}CH_2$ | $-CH(CH_3)_2$ | (A) For $C_{29}H_{41}N_9O_7S_3 \cdot 2HCl \cdot 22H_2O$<br>　　　C　　H　　N<br>Calcd. (%): 41.64　5.71　15.07<br>Found (%): 41.46　5.46　15.36<br>(B) 1780, 1760, 1670, 1625, 1540, 1455, 1380 | 1.24(6H,d,J=6Hz),0.8-2.2(11H,m),2.84(6H,s), 3.64(2H,s),3.64(2H,t,J=6Hz),3.73 and 3.92(2H, ABq,J=18Hz),4.25 and 4.49,4.30(2H, each ABq and bs,J=13Hz),4.80(2H,t,J=6Hz),4.0-5.0(1H,b), 5.13,5.16(1H, each d,J=5Hz),5.73,5.77(1H, each d.d,J=5 and 8Hz),6.58,6.63(1H, each d,J=5Hz), 6.66(1H,s),9.21,9.26(1H, each d,J=8Hz) |

EXAMPLE 6

(a) Preparation of cyclohexyloxycarbonyloxy-(cyclohexyl)methyl 7β-amino-[[[1-(2-dimethylaminoethyl)-1H-tetrazol-5-yl]thio]methyl]ceph-3-em-4-carboxylate dihydrochloride.

To 120 ml of a dimethylformamide solution containing 8.44 g of 7β-amino-3-[[[1-(2-dimethylaminoethyl)-1H-tetrazol-5-yl]thio]methyl]ceph-3-em-4-carboxylic acid dihydrochloride is added 3.34 g of potassium acetate and this solution is cooled to 0° C. With stirring, 12.3 g of cyclohexyliodomethyl cyclohexyl carbonate is added dropwise to said solution, followed by stirring at 0° C. for 5 minutes. The reaction mixture is poured into a mixture of 120 ml of methylene chloride and 120 ml of 0.1N-HCl. The aqueous layer is separated and is adjusted to pH 6.0 with a saturated aqueous sodium bicarbonate solution and extracted with methylene chloride. Water is added to the methylene chloride solution and the aqueous solution is adjusted to pH 2.0 with 4N-HCl. The aqueous layer is separated and remaining methylene chloride is removed therefrom under reduced pressure. Then, the aqueous solution is lyophilized to obtain 6.10 g of the title compound.

IR (Nujol) cm$^{-1}$:1780, 1750, 1670

(b) Preparation of cyclohexyloxycarbonyloxy-(cyclohexyl) methyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride.

To a mixture of 30 ml of water and 30 ml of methylene chloride is added 2.02 g of the compound obtained in the above (a), to which is added 0.55 g of sodium bicarbonate with stirring. The organic layer is separated and dried over anhydrous calcium chloride. After removal of the drying agent by filtration, is added to the filtrate 20 ml of a dimethylformamide solution containing 0.60 g of (2-aminothiazol-4-yl)acetic acid hydrochloride and 0.62 g of dicyclohexylcarbodiimide, followed by stirring the mixture at room temperature. The resulting precipitate is removed by filtration. To the filtrate are added 150 ml of ethyl acetate and 100 ml of ice-cooled water. The organic layer is separated, washed with water and saturated aqueous sodium chloride and dried over anhydrous magnesium sulfate. After removal of the drying agent by filtration, the filtrate is concentrated to 10 ml under reduced pressure. To the residual solution is added an anhydrous ethereal hydrogen chloride solution, and the resultant precipitate is collected by filtration to obtain 0.29 g of white powder.

This product shows the same NMR and IR spectra as those of the product obtained in Example 1.

EXAMPLE 7

Preparation of cyclohexyloxycarbonyloxy(cyclohexyl)methyl 7β-[2-(2-aminothiazol-4-yl) acetamido]-3-[[[1-(2-dimethylaminoethyl)-1H-tetrazol5-yl]thio]methyl]ceph-3-em-4-carboxylate dihydrochloride.

To a mixture of 15 ml of water and 15 ml of methylene chloride is added 1.35 g of cyclohexyloxycarbonyloxy-(cyclohexyl)methyl -7β-amino-3-[[[1-(2-dimethylaminoethyl)-1H-tetrazol-5-yl]thio]methyl]-ceph-3-em-4-carboxylate dihydrochloride obtained in Example 6(a). This mixture is stirred together with 0.30 g of sodium bicarbonate. The organic layer is separated and dried over anhydrous calcium chloride, followed by removal of the solvent by distillation under reduced pressure. The residue is dissolved in 15 ml of methylene chloride and cooled to −25° C. To this solution is added a solution of 0.5 g of 4-chloroacetoacetyl chloride in 2.0 ml of methylene chloride. The mixture is stirred at −20° C. to −15° C. for 20 minutes and then 0.76 g of thiourea and 5 ml of dimethylacetamide are added thereto. The mixture is stirred at room temperature for 3 hours. Water is added to the reaction mixture and the aqueous layer is separated, adjusted to pH 6.0 and extracted with methylene chloride. The methylene chloride solution is admixed with water and adjusted to pH 1.5 with 2NHCl. The aqueous layer is separated and remaining methylene chloride is distilled off under reduced pressure. Then, the aqueous solution is subjected to column chromatography on Diaion ® CHP-20P (75–150 μ, Mitsubishi Chemical Industries, Ltd., Japan), elution being carried out with 120 ml of 0.01N-HCl and then 20% acetonitrile-0.01N-HCl. The eluate is lyophilized to obtain 0.41 g of white powder. This product shows the same NMR and IR spectra as those of the product obtained in Example 1.

EXAMPLE 8

(a) Preparation of cyclohexyloxycarbonyloxy-(cyclohexyl) methyl 7β-[2-(2-aminothiazol-4-yl)acetamido]3-acetoacetoxymethylceph -3-em-4-carboxylate.

In 30 ml of N,N-dimethylformamide is dissolved 4.76 g of sodium 7β-[2-(2-aminothiazol-4-yl)acetamido]-3-acetoacetoxymethylceph-3-em-4-carboxylate and the solution is cooled to −5° C. With stirring, to the solution is added dropwise 6.2 g of cyclohexyliodomethyl cyclohexyl carbonate, followed by stirring for further 5 minutes. The reaction mixture is poured into a mixture of 300 ml of ethyl acetate and 200 ml of ice water and the organic layer is separated. The aqueous layer is extracted with 200 ml of ethyl acetate. The organic layers are combined and washed with 150 ml each portion of ice water (three times) and saturated aqueous sodium chloride (three times) and then dried over anhydrous magnesium sulfate. The solution is then distilled off under reduced pressure and isopropyl ether is added to the residue. The resultant white powder is collected by filtration, washed with isopropyl ether and dried to obtain 3.73 g of the title compound.

IR (KBr) cm$^{-1}$:1780, 1750, 1680

(b) Preparation of cyclohexyloxycarbonyloxy-(cyclohexyl) methyl 7β-[2-(2-aminothiazol-4-yl)acetamido-3-[[[1-(2-dimethylaminoethyl)-1H-tetrazol-5-yl]thio]-methyl]ceph-3-em-4-carboxylate dihydrochloride.

To 30 ml of an acetone solution containing 2.6 g of the compound obtained in the above (a) is added 10 ml of an aqueous solution containing 0.8 g of sodium bicarbonate and 0.9 g of 1-(2-dimethylaminoethyl)-5-mercapto-1H-tetrazole. The mixture is heated at 40° C. for 1 hour with stirring. The reaction mixture is poured into a mixture of 150 ml of ethyl acetate and 50 ml of ice water and the organic layer is separated, washed with ice water and then with saturated aqueous sodium chloride. This is then dried over anhydrous magnesium sulfate and thereafter the solvent is distilled off under reduced pressure. The residue is dissolved in 20 ml of 0.1N-HCl and subjected to column chromatography on Diaion ® CHP-20P (75–150 μ, Mitsubishi Chemical Industries,Ltd., Japan), elution being carried out with 0.01N-HCl and then with 20 v/v % acetonitrile-0.01N-HCl. The eluate is lyophilized to obtain 0.043 g of white powder which is the title compound.

This product shows the same NMR and IR spectra as those of the product obtained in Example 1.

FORMULATION EXAMPLE 1

419.5 g (250 g in terms of the non-ester compound) of cyclohexyloxycarbonyloxy-(cyclohexyl) methyl 7β-[2-(2-aminothiazol-4-yl)acetamido]-3-[[[1(2-dimethylaminoethyl-1H-tetrazol-5-yl)thio]methyl]ceph-3-em-4-carboxylate dihydrochloride obtained in Example 1 is evenly admixed with 70.5 g of hydroxypropylcellulose and 70.5 g of carboxymethylcellulose and the mixture is distributed in 280.2 mg (125 mg in terms of the non-ester compound) portions into capsules in a conventional manner.

FORMULATION EXAMPLE 2

419.5 g (250 g in terms of the non-ester compound) of cyclohexyloxycarbonyloxy-(cyclohexyl) methyl 7β-[2-(2-aminothiazol-4-yl)acetamido]-3-[[[1(2-dimethylaminoethyl-1H-tetrazol-5-yl]thio]methyl]ceph-3-em-4-carboxylate dihydrochloride obtained in Example 1 is evenly admixed with 70 g of starch and 6 g of hydroxypropylcellulose and the mixture is tableted in a conventional manner to provide 247.8 mg tablets (125 mg in terms of the non-ester compound).

EXPERIMENTAL EXAMPLE

The compounds of Examples 1, 2 and 3 and, as a control compound, the 1-(ethoxycarbonyloxy)ethyl ester of compound [II], i.e. 1-(ethoxycarbonyloxy) ethyl 7β-[2-(2-aminothiazol-4-yl)-acetamido]-3-[[[1(2-dimethylaminoethyl)-1H-tetrazol-5-yl]thio]methyl]ceph-3-em-4-carboxylate (hereinafter referred to as compound A) are administered orally to mice, each compound to one animal, in the dose of 100 mg/kg (in terms of non-ester form thereof, i.e. compound [II]). At 0.25, 0.5, 1.0 and 2.0 hours after administration, the concentration of compound [II] in plasma of the mouse is measured by the cup method using *Proteus mirabilis Eb* 313 as the test organism and the area under plasma concentration-time curve from zero to 2 hours (AUC) is calculated.

Control test

The compound [II] was subcutaneously applied and AUC was calculated in the same manner as above.

The bioavailability defined in the following formula is shown in the Table 3.

$$\text{Bioavailability (\%)} = \frac{AUC(\text{oral administration})}{AUC(\text{subcutaneous administration})} \times 100$$

TABLE 3

| Compound No. (Example No.) | Bioavailability (%) |
|---|---|
| 1 | 65.6 |
| 2 | 60.0 |
| 3 | 63.0 |
| Compound A | 23.9 |

We claim:

1. A compound of the formula:

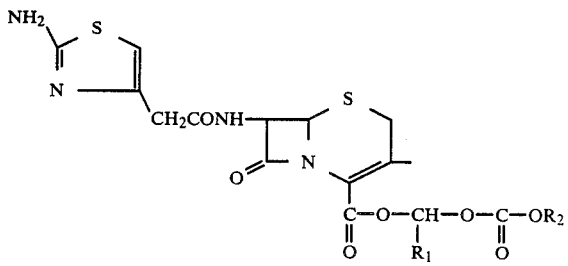
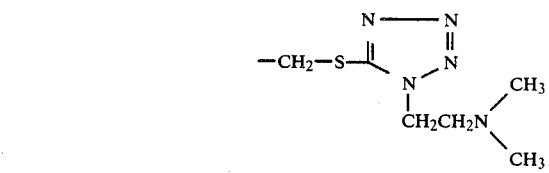

wherein $R_1$ is a cycloalkyl having 5-7 carbon atoms group; and $R_2$ is a cycloalkyl having 5-7 carbon atoms, or a pharmaceutically acceptable salt thereof.

2. A compound according to claim 1, wherein $R_1$ is a cyclohexyl; and $R_2$ is cyclohexyl or cyclopentyl.

3. A compound according to claim 1, wherein the pharmaceutically acceptable salt is hydrochloride.

4. A compound according to claim 1, the compound of the formula being cyclohexyloxycarbonyloxy-(cyclohexyl)methyl 7β-[2-(2-aminothiazol-4-yl)acetamido]-3[[[1-(2-dimethylaminoethyl)-1H-tetrazol-5-yl]thio]methyl]ceph-3-em-4-carboxylate.

5. A pharmaceutical composition comprising a compound of the formula:

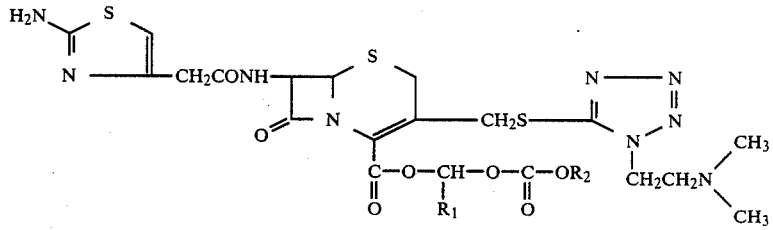

wherein $R_1$ is a cycloalkyl having 5-7 carbon atoms group; and $R_2$ is a cycloalkyl having 5-7 carbon atoms, or a pharmaceutically acceptable salt thereof as an effective ingredient.